US010521906B2

(12) United States Patent
Forman et al.

(10) Patent No.: US 10,521,906 B2
(45) Date of Patent: Dec. 31, 2019

(54) METHOD AND IMAGE PROCESSOR FOR EVALUATING A CONTRAST AGENT-ENHANCED MAGNETIC RESONANCE SLICE IMAGE OF A HEART (71) Applicant: Siemens Healthcare GmbH, Erlangen (DE)

(72) Inventors: Christoph Forman, Erlangen (DE); Tanja Kurzendorfer, Trautmannshofen (DE); Alexander Brost, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 122 days.

(21) Appl. No.: 15/907,592

(22) Filed: Feb. 28, 2018

(65) Prior Publication Data
US 2018/0253844 A1 Sep. 6, 2018

(30) Foreign Application Priority Data

Mar. 1, 2017 (DE) .......................... 10 2017 203 313

(51) Int. Cl.
*A61B 6/03* (2006.01)
*A61B 5/055* (2006.01)
(Continued)

(52) U.S. Cl.
CPC .......... *G06T 7/0012* (2013.01); *A61B 5/055* (2013.01); *A61K 49/06* (2013.01);
(Continued)

(58) Field of Classification Search
CPC .. G06K 9/00; G06T 7/00; G01R 33/20; A61B 5/055
(Continued)

(56) References Cited

U.S. PATENT DOCUMENTS

2010/0085051 A1\* 4/2010 Littmann ................ A61B 5/055 324/309
2011/0158496 A1\* 6/2011 Ciofolo-Veit ............. G06T 7/11 382/131

OTHER PUBLICATIONS

Karim et al., "Evaluation of state-of-the-art segmentation algorithms for left ventricle infarct from late Gadolinium enhancement MR images," Medical Image Analysis, vol. 30, pp. 95-107 (2016).

(Continued)

*Primary Examiner* — Abolfazl Tabatabai
(74) *Attorney, Agent, or Firm* — Schiff Hardin LLP (57) ABSTRACT In a method and processor for evaluating a contrast agent-enhanced two-dimensional magnetic resonance slice image of a heart of a patient in order to determine picture elements revealing contrast agent deposits in the myocardium, an endocardium contour in the magnetic resonance slice image, taking into consideration deposition information describing picture elements potentially revealing contrast agent deposits and determined by image analysis on the basis of a shape assumption for the heart structure that is to be examined, in particular the left ventricle, such that picture elements potentially revealing contrast agent deposits are avoided as much as possible as a contour component. An epicardium contour enclosing the endocardium contour is then determined. Picture elements are marked that indicate contrast agent enhancement in the myocardium lying between the epicardium contour and the endocardium contour as contrast agent deposit.

20 Claims, 5 Drawing Sheets (51) Int. Cl.
- *G06T 7/00* (2017.01)
- *G06T 7/13* (2017.01)
- *G06T 7/155* (2017.01)
- *G16H 50/20* (2018.01)
- *G16H 30/40* (2018.01)
- *A61K 49/06* (2006.01)
- *G01R 33/48* (2006.01)
- *G01R 33/56* (2006.01)
- *G06K 9/62* (2006.01)
- *G06T 15/08* (2011.01)
- *G06T 19/20* (2011.01)
- *G06K 9/00* (2006.01)
- *G06K 9/46* (2006.01)
- *G06T 7/12* (2017.01)
- *G06T 7/168* (2017.01)
- *G01R 33/483* (2006.01)

(52) U.S. Cl.
CPC ..... *G01R 33/4824* (2013.01); *G01R 33/5601* (2013.01); *G01R 33/5608* (2013.01); *G06K 9/0014* (2013.01); *G06K 9/4604* (2013.01); *G06K 9/4638* (2013.01); *G06K 9/6229* (2013.01); *G06K 9/6268* (2013.01); *G06T 7/12* (2017.01); *G06T 7/13* (2017.01); *G06T 7/155* (2017.01); *G06T 7/168* (2017.01); *G06T 15/08* (2013.01); *G06T 19/20* (2013.01); *G16H 30/40* (2018.01); *G16H 50/20* (2018.01); *A61B 2576/023* (2013.01); *G01R 33/4835* (2013.01); *G06T 2207/10096* (2013.01); *G06T 2207/20061* (2013.01); *G06T 2207/20081* (2013.01); *G06T 2207/20116* (2013.01); *G06T 2207/30048* (2013.01)

(58) Field of Classification Search
USPC .......................................................... 382/131
See application file for complete search history.

(56) References Cited

OTHER PUBLICATIONS

Kurzendorfer et al., "Semi-Automatic Segmentation and Scar Quantification of the Left Ventricle in 3-D Late Gadolinium Enhanced MRI," 32nd Annual Scientific Meeting of the ESMRMB, (ESMRMB 2015, Edinburgh, 1-3, 10), pp. 318-319 (2015).

Albà et al., "Automatic Cardiac LV Segmentation in MRI Using Modified Graph Cuts with Smoothness and Interslice Constraints," Magnetic Resonance in Medicine, vol. 72, pp. 1775-1784 (2014).

Shin et al., "Rapid Single-Breath-Hold 3D Late Gadolinium Enhancement Cardiac MRI Using a Stack-of-Spirals Acquisition," Journal of Magnetic Resonance Imaging, vol. 40, pp. 1496-1502 (2013).

Ringenberg et al., "Automated segmentation and reconstruction of patient-specific cardiac anatomy and pathology from in vivo MRI," Measurement Science and Technology, vol. 23, No. 12, pp. 1-13 (2012).

Marquez-Neila et al., "A Morphological Approach to Curvature-Based Evolution of Curves and Surfaces," IEEE Transactions on Pattern Analysis and Machine Intelligence, vol. 36, No. 1, pp. 2-17 (2014).

* cited by examiner

METHOD AND IMAGE PROCESSOR FOR EVALUATING A CONTRAST AGENT-ENHANCED MAGNETIC RESONANCE SLICE IMAGE OF A HEART

BACKGROUND OF THE INVENTION

Field of the Invention

The invention concerns a method for evaluating a contrast agent-enhanced two-dimensional magnetic resonance slice image of a heart of a patient in order to determine picture elements revealing contrast agent deposits in the myocardium, as well as to an image processor, and an electronically readable data medium that implement such a method.

Description of the Prior Art

Imaging based on the use of contrast agent is a technique employed for a variety of purposes in medical engineering. An important field of application in this context is the administration of contrast agent such that it accumulates in certain regions of the body that are to be assessed, for example, lesions. A clinical application example is the localization of scar tissue/fibroses in the heart on the basis of contrast agent deposits, gadolinium being used here as the contrast agent in most cases. The acquisition of corresponding magnetic resonance images is usually also referred to as "late gadolinium-enhanced" imaging (LGE imaging). A corresponding acquisition method is known for example from an article by Shin et al., "Rapid single-breath-hold 3D late Gadolinium enhancement cardiac MRI using a stack-of-spirals acquisition", JMRI 40: 1496-1502 (2013). For interventions or operations that are scheduled to be performed, such as minimally invasive electrophysiology procedures, the information pertaining to the position of the myocardium and the location of the scar tissue is extremely important. However, it is difficult to obtain this information automatically from a corresponding LGE magnetic resonance slice image.

In this context it is known to acquire slice stacks of two different types of magnetic resonance images in the short-axis direction, specifically a slice stack for the anatomical information (typically time-resolved CINE images) and a slice stack acquired with contrast agent enhancement, in particular as LGE slice images, in order to obtain the scar tissue information. In the CINE slice images, the myocardium is segmented and the corresponding anatomy is registered to the LGE image data in order to obtain the scar tissue information or general contrast agent deposition information.

However, there are many problems with this approach, in particular with regard to the registration and fitting of the CINE magnetic resonance data to the LGE magnetic resonance data. Thus, in the first instance, the global position of the heart may change during the scan due to patient motion. It is possible that the cardiac phases of the CINE slice stack do not exactly correspond to those of the LGE slice stack. Displacements between individual slices may result due to multiple breath-hold cycles. Even if such displacements may appear trivial, they can lead to significant errors in the quantification of scar tissue in the myocardium.

For this reason, the assessment of the scar tissue is carried out purely manually in the majority of medical institutions, for example hospitals, based solely on the slice stack of two-dimensional magnetic resonance slice images obtained by LGE imaging. Automated methods have been proposed in the prior art, though they are heavily dependent on an accurate segmentation of the myocardium, cf. in this regard, for example, the article by Rashed Karim et al., "Evaluation of state-of-the art segmentation algorithms for left ventricle infarct from late Gadolinium enhancement MR images", Medical Image Analysis 30 (2016): 95-107.

Approaches that refer to the segmentation of the anatomy and of the scar tissue from a single contrast agent-enhanced magnetic resonance image dataset have previously been proposed only for the case of three-dimensional magnetic resonance image data. An example is the procedure described in the article by Tanja Kurzendorfer et al., "Semi-Automatic Segmentation and Scar Quantification of the Left Ventricle in 3-D Late Gadolinium Enhanced MRI", ESMRMB 2015, pages 318 to 319.

SUMMARY OF THE INVENTION

An object of the invention is to provide a solution for the automated localization of the myocardium and of contrast agent accumulations in the myocardium, for contrast agent-enhanced two-dimensional magnetic resonance slice images.

In order to achieve this object, a method of the type cited in the introduction comprises the following steps according to the invention:

In a computer, determining an endocardium contour in the magnetic resonance slice image, taking into consideration deposition information describing picture elements potentially revealing contrast agent deposits and determined by image analysis on the basis of a shape assumption for the heart structure that is to be examined, in particular the left ventricle, such that picture elements potentially revealing contrast agent deposits are avoided as much as possible as a contour component.

Also in the computer, determining an epicardium contour enclosing the endocardium contour.

Also in the computer, marking picture elements indicating contrast agent enhancement in the myocardium lying between the epicardium contour and the endocardium contour as contrast agent deposit.

The slice image with the marked picture elements is made available from the computer in electronic form as a data file.

According to the invention, a two-dimensional magnetic resonance slice image of the heart, in particular a short-axis magnetic resonance slice image, is taken as a starting point. In this slice image, each picture element, i.e. each pixel, is assigned an image value as image information. In this case, when gadolinium is used as the contrast agent for example, image values exhibiting high intensities may indicate high concentrations of contrast agent. The contrast agent, for example gadolinium, forms a deposit, for example on scar tissue, partially within the myocardium, while the blood within the substructure of the heart that is to be studied, in particular the left ventricle, is also clearly recognizable in the magnetic resonance slice image. The challenge that presents itself when it comes to the segmentation is, as has been recognized, that due to the deposition of contrast agent in the myocardium, the (in principle) substantially circular blood pool in the substructure of the heart is "disaggregated", which makes the conventional approaches to segmentation in two dimensions significantly more difficult. It is therefore proposed to have recourse to the basic knowledge concerning the shape—the assumed shape—of the heart structure that is to be examined, and the knowledge about the fact that contrast agent deposits may exist, in order to utilize the same in the determination of an improved endocardium contour and to facilitate automation. In this case, an estimated contour, which may be produced from the shape assumption, is taken as the starting point in order then to refine this using the deposition information.

As a result of the fully automatic procedure for segmentation both of the anatomy and of the deposits, i.e. in particular of the scar tissue, from a single contrast agent-enhanced magnetic resonance slice image, in particular an LGE magnetic resonance slice image, neither a registration of two different scans nor a manual interaction and segmentation is necessary. This yields a number of advantages. Firstly, the use of a single magnetic resonance sequence reduces the risk of overlooking relevant scar tissue, thus enabling a precise quantification of scar tissue to be made. Secondly, no registration of different scans is required, since all the information can be obtained from a single dataset. Thirdly, the automatic segmentation of the deposits, ultimately, therefore, of the scar tissue information, avoids the additional effort required for a manual segmentation, thereby opening up wide-ranging application possibilities in the clinical routine.

In an embodiment of the present invention, initially, in order to determine the contours, a localization of the substructure is carried out using background information describing a circular shape of the substructure, in particular the left ventricle. In this exemplary embodiment, the assumed shape is therefore described as background information that exploits the knowledge that in particular in the case of short-axis magnetic resonance slice images, relevant substructures, in this instance the left ventricle, appear substantially round, with the result that a rough localization of the substructure can take place in a particularly simple manner by searching for suitable circular structures as a potential blood pool within the substructure. In an exemplary, preferred embodiment, the substructure is detected using circular Hough transforms and/or a circularity measure.

In another embodiment, an edge detection algorithm, for example a Canny algorithm, is used initially in order to extract edges from the magnetic resonance slice image. In a further substep, circular Hough transforms are applied, in which case it is preferred to choose the radii of the circular Hough transforms in a predefined radial range in which the radius of the interior of the substructure may lie, with a predefined increment. For example, it can be provided to make use of a radial range of 17 mm to 35 mm with an increment of 2 mm in order to localize the left ventricle. The most suitable candidate is then assumed as describing the blood pool in the substructure.

In another embodiment, an additional circularity measure may be applied in order to validate this position of the substructure. Otsu thresholding can be performed in this case on the entire magnetic resonance slice image in order to convert the image into a binary mask. Objects that are smaller than a predetermined threshold value are removed, while the circularity of the remaining objects is estimated. If the center points of the roundest object and the result of the circular Hough transforms lie within a predetermined distance range, it is assumed that the substructure, in particular the left ventricle, has been accurately detected.

In another embodiment of the present invention, in order to determine the endocardium contour, an estimated contour is first determined by localization of the blood within the left ventricle, which estimated contour is used for determining the deposition information. Therefore first an estimated contour for the endocardium is used, in order to determine the deposition information by which a refinement can then be carried out, resulting in the endocardium contour. Consequently, a rough estimation is combined with background knowledge in order to permit an at least rough estimation of the location of deposits, in particular scar tissue, and thus to enable a more accurate endocardium contour to be segmented.

Whereas an estimated contour may basically be determined by various algorithms, for example a random walk algorithm, in a preferred embodiment the estimated contour is determined by a morphologically active evolution algorithm for a contour curve, in particular without taking edges into consideration. Preferably, during localization of the substructure, also of the blood within the substructure, a center point of the substructure is taken as starting point for the evolution algorithm. As already noted, this localization of the substructure is preferably carried out on the basis of the assumed shape and the clearly visible blood pool, in particular when Hough transforms are used. With particular advantage, taking edges into consideration is intentionally avoided initially in this case, and a morphological active evolution algorithm for a contour curve without consideration of edges (morphological active contours algorithm without edges—MACWE algorithm) is used. This is because the edges may be blurred by the potential deposits.

In another embodiment, a MACWE algorithm is used as a rough estimation of a boundary of the blood pool within the substructure, for which reference may be made by way of example to the article by P. Márquez-Neila, "A morphological approach to curvature-based evolution of curves and surfaces", Pattern Analysis and Machine Intelligence, IEEE Transactions on, 2014, 36 (1): 2-17. It is pointed out in this case that this approach on its own is not enough to determine a sufficiently accurate endocardium contour, since the transition between the blood pool and the deposits, in particular scar tissue, may be very gentle or smooth. The MACWE algorithm nevertheless provides a rough basis, which already represents an improvement compared to a purely edge-based approach, and which may serve as a basis for the subsequent refinement. It should also be noted that, with regard to the evolution algorithm, certain possible extension regions of the substructure may be predefined, in particular regions of the left ventricle.

In another embodiment of the invention, an inner region within the estimated contour and an outer region surrounding the estimated contour are defined in order to determine the deposition information. Picture elements in the outer region, which exceed a threshold value determined by statistical evaluation of the image values of the picture elements in the inner region, are marked as potentially containing contrast agent deposits. In clinical practice, it has proven beneficial for the threshold value to be determined as the sum of the mean value of the image values of the inner region and the standard deviation of the image values of the inner region. Preferably, therefore, the average intensity and the standard deviation in the blood pool described by the estimated contour are determined in the first instance, wherein all picture elements, i.e. pixels, lying in the outer region that have a greater intensity than the correspondingly defined threshold value are marked as potentially containing deposits. Thus, for example, a kind of binary deposition map can be produced in which all picture elements potentially revealing deposits are marked with "1", others with "0".

It is of particular advantage in this context if, starting from a picture element whose image value exceeds the threshold value, all picture elements following in a radially outward direction are likewise marked as potentially containing contrast agent deposits. This is based on the simple assumption that if it is already accepted that contrast agent deposits/ scar tissue are present at a particular point, then blood pool also cannot follow again in the radially outward direction. It has furthermore proven beneficial in preparation for following steps, which will be discussed in more detail later, to determine the deposition information in polar coordinates, in which case the center point of the localized substructure is beneficially used as the origin of the polar coordinate system.

For following steps of the method according to the invention in many embodiments, as will be explained in detail below, it is also beneficial to have available further information more accurately describing the location of edges or the probability of belonging to a contour in addition to the deposition information, which is preferably present in the form of a deposition map, in order finally to determine the endocardium contour taking said information into consideration. The use of a classifier (classification algorithm) may prove helpful in determining supplementary information of this type, but also in determining the deposition information.

Accordingly, in another embodiment of the present invention, candidate picture elements for contour points are defined from the estimated contour, by equidistant point selection along radial rays with respect to the substructure. In order to determine the deposition information and/or probability information containing probability values describing the probability for belonging to the endocardium contour, an endocardium classifier, which emits at least one output value describing the potential belonging to a contrast agent deposit and/or a probability value, is applied to each candidate picture element. In this case it is preferred, if a classification algorithm trained by machine learning, such as a random forest algorithm, is used as the endocardium classifier, to then use training slice images with associated known fundamental truths as training data for training the classification algorithm. In this case, it is preferred to use the endocardium classifier for determining the probability information, since a large amount of annotated training data, which therefore contains endocardium contours as fundamental truth, already exists. It is also conceivable to determine the deposition information, for example as a value describing the probability for belonging to a contrast agent deposit, by the use of such an endocardium classifier when suitable training data is available. It is furthermore generally beneficial if the endocardium classifier evaluates at least one property referred to the intensity and/or at least one gradient of the considered candidate picture element and/or an environment encompassing the considered candidate picture element.

In a further embodiment potential candidate picture elements, which could be part of the endocardium contour, are first defined on the basis of the estimated contour. In this case, N equidistant points, i.e. picture elements, are beneficially defined on the basis of radial rays which emanate from the center point of the substructure and cross through the estimated contour, while known anatomical extensions of the substructure are beneficially referred to in order to limit the number of candidate picture elements. The endocardium classifier is then applied to the candidate picture elements or their image values and environments, which classifier is able, for example, to evaluate sixteen properties of the candidate picture element and its environment, based on the local intensity and the gradient. The corresponding property vector is in this case of course also used in the machine learning of the endocardium classifier, which is preferably embodied as a random forest classification algorithm.

Ideally, after the endocardium classifier has been used, the probability information and the deposition information are available, the former preferably in the form of a probability map, the latter preferably in the form of a deposition map, both in turn preferably in polar coordinates, with the endocardium contour being determined based on this information preferably by means of a cost estimation. As an alternative to determining probability information, it is also possible to determine edge information, i.e. to detect edges within the magnetic resonance slice image, and to generate an edge map by assigning the value "1" to picture elements at which an edge is present, and the value "0" to picture elements at which no edge is present.

In any case, in preferred embodiment of the present invention, in order to determine the endocardium contour from determined edge information describing the position of edges in the magnetic resonance slice image and/or from the probability information determined as described as well as from the deposition information, a cost map is determined by which a path preferring edges or high probability values and avoiding contrast agent deposits according to the deposition information is identified as an endocardium contour. The idea is therefore to combine the deposition information and the edge information/the probability information to produce a common cost map so that a path finding algorithm can locate the endocardium contour as accurately as possible using a cost-based approach. In the case of the use of edge information and the deposition information, paths along edges, but which are not potentially assigned to deposits, are therefore preferred; in the case of the probability information, paths are preferred that with most likelihood were classified as belonging to the endocardium contour. In this case it has proven particularly advantageous if the cost map is determined in a polar coordinate system referred to a center point of the substructure, in particular a center point chosen on account of the estimated contour and/or the localization, the path searched for along the polar angle being chosen as short as possible. In a polar coordinate system, only one path from one side of the map to the other side of the map along the polar angle needs to be found in order to be able to locate a complete boundary of the substructure, in particular of the left ventricle. Beneficially, a minimum cost path (MCP) algorithm with path length weighting may be used as the path finding algorithm for this purpose. Costs in the cost map therefore result for example as "1" for picture elements potentially revealing contrast agent deposits and non-edge picture elements, or, if probability information is used, as "1" for picture elements potentially revealing contrast agent deposits and "1 minus the probability value" for other picture elements. Naturally, other costs may also be estimated, for example different costs for edges and potential contrast agent deposits and/or the costs according to the deposition information may also be different, for example formulated as a value indicating probabilities, in particular if an endocardium classifier is also used for this purpose.

It is conceivable within the scope of the present invention to choose, as the epicardium contour, a scaled endocardium contour surrounding the former at a distance, though there is little preference for this.

Accordingly, a preferred embodiment of the present invention provides that in order to determine the epicardium contour, further information, likewise based on edge information and/or further probability information determined by means of an epicardium classifier or the cost map is used, wherein a path preferring edges or high probability values, in the case of the use of the polar coordinate system the shortest possible path, is used as the epicardium contour. In principle, therefore, the above description concerning the endocardium also applies in relation to the determining of the epicardium contour, except that in this case the constraints on the basis of deposition information cease to apply. A learning epicardium classifier may also be employed in respect of the epicardium contour. Beneficially, the map is considered limited to a search area for the epicardium on the basis of the known, basically possible extensions of the epicardium. A random forest classification algorithm can preferably be used also for the epicardium classifier, and then an MCP algorithm in polar coordinates with path length weighting can be applied.

In an advantageous development of the present invention it can be provided that the epicardium contour and/or the endocardium contour are/is smoothed. A smoothing of the contours determined in each case is beneficial to the effect that smaller, still remaining corners can be excluded and/or papillary muscles close to the boundary of the endocardium, for example in the endocardium contour, may still be included. For example, the convex hull of the initially determined contours can be determined and used as a new contour.

If it is only through the epicardium contour and the endocardium contour that the location of the myocardium is known as lying between said contours, the picture elements in the myocardium that are to be assigned to contrast agent deposits, i.e. between the contours, can be determined by a threshold value comparison with a predefined threshold value and/or a threshold value determinable as a function of acquisition parameters and/or image parameters of the magnetic resonance slice image and/or of a user input. This is already generally known in the prior art and does not need to be explained here in more detail.

As already mentioned, the magnetic resonance slice image is preferably a short-axis magnetic resonance slice image. The present invention can equally be applied with particular advantage also to a slice image stack, which means that a number of magnetic resonance slice images of a slice image stack, in particular one covering the heart from its base up to the apex, can be evaluated. It is preferred in this case to make reference to a magnetic resonance slice image relating to a middle slice of the heart as the first magnetic resonance slice image to be considered, since the substructure, in particular the left ventricle, as well as the epicardium contour and the endocardium contour, can be particularly easily and robustly determined in this case. Results of this first segmentation carried out can then be apically and basally propagated in each case starting from the middle slice and can be drawn upon for example as starting values for segmentations to be performed there in order to increase the robustness accordingly. Results of a first considered magnetic resonance slice image of the slice stack are therefore applied to other magnetic resonance slice images of the magnetic resonance slice image stack in particular in order to determine initial values.

Beneficially, an output image can be generated and/or displayed in which the epicardium contour and/or the endocardium contour and/or visualization elements indicating picture elements marked as contrast agent deposit are added to the magnetic resonance slice image. In this way, the determined information can be communicated to a viewer in a particularly easy and intuitive manner.

In addition to the method, the present invention also concerns an image processor having a computer designed (configured) to perform the method according to the invention. In this case the image processor may also be provided as part of a magnetic resonance device or magnetic resonance system. All statements made with respect to the inventive method apply to the inventive image processor, such that the same advantages are obtained. The image processor may include contour determining units for determining the endocardium contour and the epicardium contour and a marking unit (circuit) for marking picture elements revealing contrast agent deposit.

The present invention also encompasses a non-transitory, computer-readable data storage medium encoded with programming instructions that, when the storage medium is loaded into an image processing computer, cause the image processing computer to execute any or all embodiments of the method according to the invention, as described above.

DESCRIPTION OF THE PREFERRED EMBODIMENTS

The present invention shall be explained in more detail below with reference to two exemplary embodiments, which differ with regard to the determining of possible candidates for the delimiting of the endocardium and of the epicardium. Taken as starting point in both exemplary embodiments is a short-axis LGE magnetic resonance slice image, i.e. a two-dimensional magnetic resonance image of the heart of a patient acquired in the short-axis direction, gadolinium having been administered beforehand as contrast agent, which, in the presence of scar tissue or fibroses, accumulates in the myocardium at such sites and basically makes automatic segmentation of the myocardium more difficult, since high image values, i.e. intensities, occur not only due to the blood pool of the left ventricle discussed here as a substructure of the heart, but also in the directly adjoining myocardium.

Figure 1:
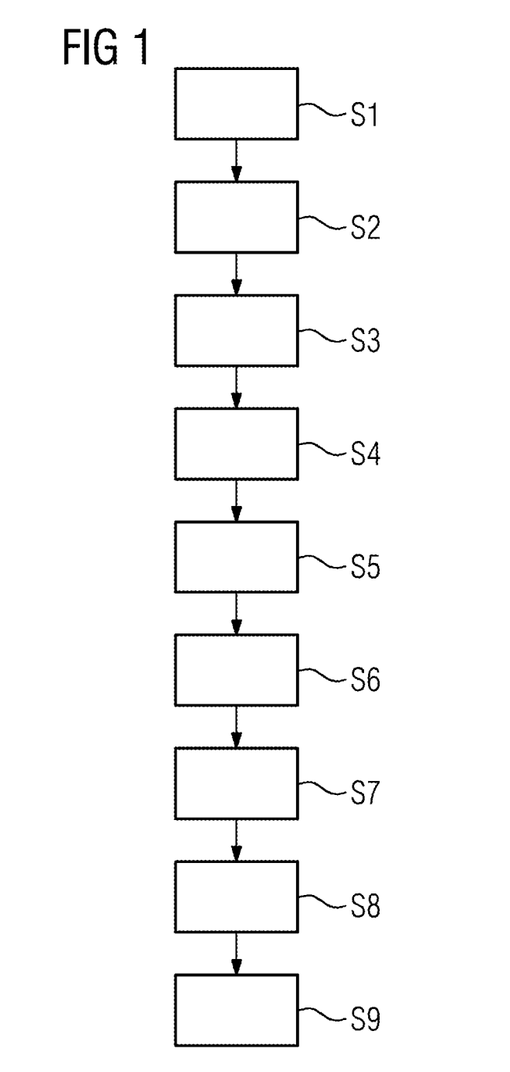
FIG. 1 is a flowchart of a first exemplary embodiment of the method according to the invention.

According to a step S1, cf. FIG. 1, the left ventricle is first detected in the magnetic resonance slice image and therefore localized. If an entire slice stack of magnetic resonance slice images covering the heart from the base of the heart to the apex is considered, the middle slice is preferably used as the starting point. Circular Hough transforms are then applied to the two-dimensional magnetic resonance slice image after an edge detection algorithm, in particular a Canny algorithm, has been used for filtering the magnetic resonance slice image. The radius for the circular Hough transform is chosen in a range of 17 mm to 35 mm with an increment of 2 mm, anatomical heart information according to the literature having been drawn upon for selecting these values. With the detection of the left ventricle on account of its circular shape, there is also yielded a center point of the left ventricle, which, if a slice stack is present, can be applied to the remaining magnetic resonance slice images that are processed in subsequent passes.

In a step S2, the position of the left ventricle, which finally has been detected on account of its blood pool, is used in order to determine the boundary of the blood pool and hence of the endocardium roughly in the first instance as an estimated contour. In this case, starting from the center point of the left ventricle on account of the localization, an evolution algorithm is applied which employs a morphological active contours approach without edges (MACWE algorithm), which therefore requires no clearly defined borders, since the termination of the evolution of the contour is not dependent on edges. Instead, the MACWE algorithm uses image statistics from the inside as well as from the outside of the contour. A circle having a radius of e.g. ten picture elements around the detected center point of the left ventricle may be chosen as the start contour of the evolution algorithm, it being possible to stop the MACWE algorithm after a heuristically chosen number of fifteen iterations.

Figure 2:
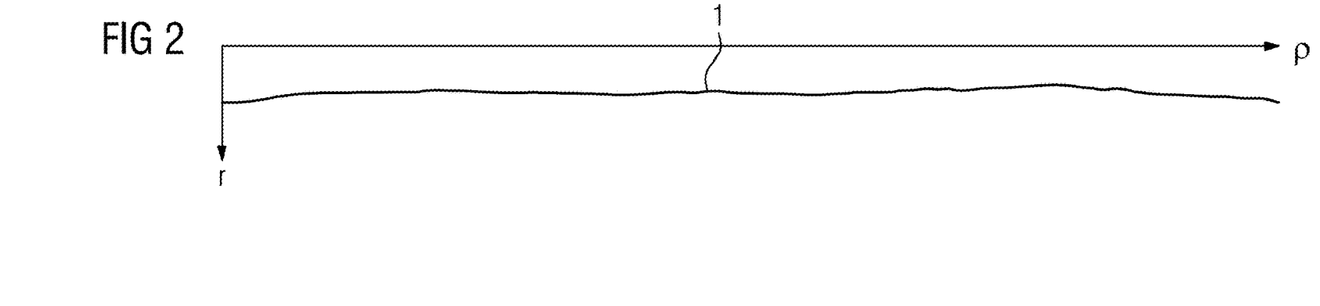
FIG. 2 shows an estimated contour for a magnetic resonance slice image in polar coordinates.

An example of an estimated contour resulting in this way is shown in FIG. 2, already in polar coordinates, which refer to the center point of the localized left ventricle, where r denotes the radius, $\rho$ the polar angle.

In a step S3, cf. once again FIG. 1, starting from such an estimated contour 1, following a determination of the magnetic resonance slice image in polar coordinates, edge information for the magnetic resonance slice image is determined in polar coordinates, a Canny algorithm again being determined in the present case as an edge detection algorithm. A Gaussian smoothing may be used to extract smaller corners. An edge map resulting in this way, wherein picture elements marked in black correspond to an edge, is shown in FIG. 3, once again in polar coordinates.

Figure 4:
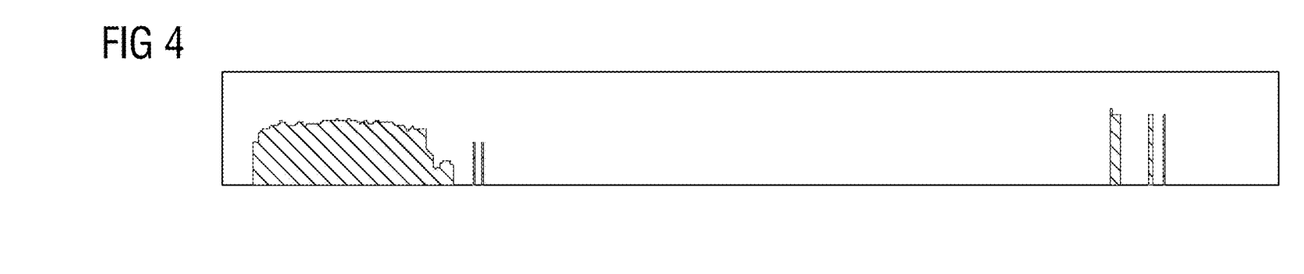
FIG. 4 shows a deposition map for the magnetic resonance image in polar coordinates.

In a step S4, the order of steps S3 and S4 being freely selectable, the magnetic resonance slice image is again used in polar coordinates in order to determine deposition information that marks picture elements in which a contrast agent deposit is potentially present, i.e. scar tissue, for example. To that end, reference is once again made to the estimated contour 1, which subdivides the magnetic resonance slice image into an outer region and an inner region. For the inner region, the mean value of the image values and the standard deviation from said mean value are determined. A threshold value is determined as the sum of the mean value and the standard deviation. All picture elements in the outer region that have an image value exceeding the just defined threshold value are marked as potentially having contrast agent deposits, exactly like all picture elements following such a picture element in the radially outward direction. In this way, a deposition map, as shown in FIG. 4 by way of example, is produced as deposition information.

Figure 3:
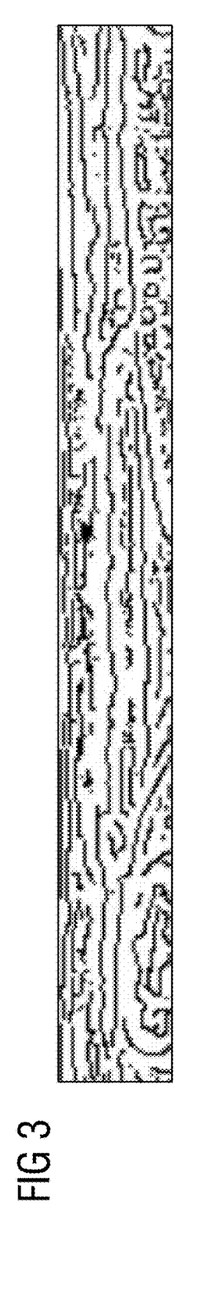
FIG. 3 shows an edge map for the magnetic resonance image in polar coordinates.
Figure 5:
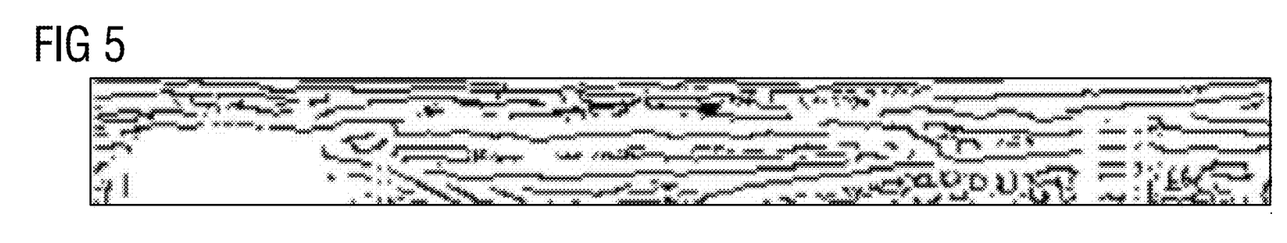
FIG. 5 shows a cost map as a combination of the edge map and the deposition map.

In a step S5, the edge map of step S3 and the deposition map of step S4 are then merged to form a cost map, as shown by way of example in FIG. 5. In this cost map, each pixel, i.e. picture element, lying on an edge and not marked as potentially containing contrast agent deposits is then assigned the cost value "0", all other picture elements being assigned the cost value "1".

Figure 6:
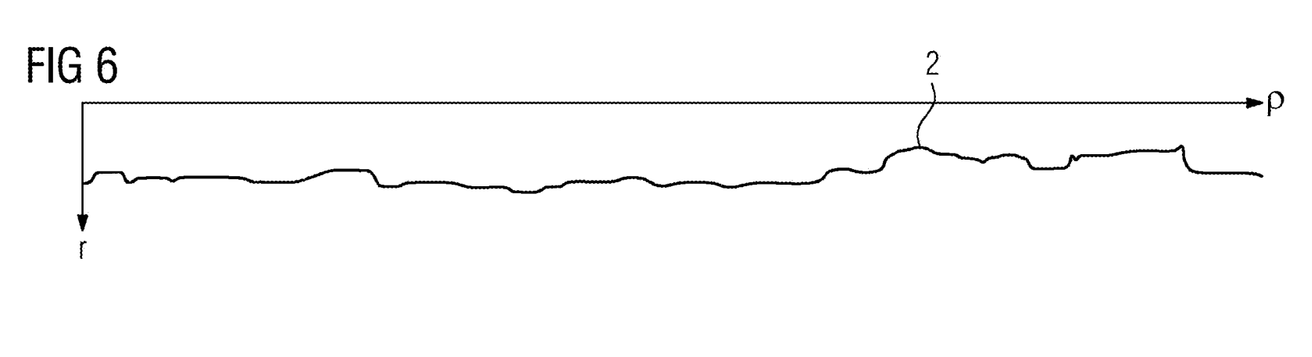
FIG. 6 shows an endocardium contour in polar coordinates, derived from the cost map of FIG. 5.

In a step S6, the cost map, as shown by way of example in FIG. 5, is then used in order to determine a refined endocardium contour by means of an evolution algorithm which searches for the most cost-effective and shortest path through the cost map, in other words along the polar angle $\rho$ from one side of the cost map to the other, in order to obtain a closed endocardium contour. In practice, therefore, an MCP algorithm with length weighting is used as the evolution algorithm. An exemplary endocardium contour 2 resulting in such a way is shown in polar coordinates in FIG. 6. The endocardium contour can then be added in Cartesian coordinates and/or smoothed by determining the convex hull for the determined contour points.

In a step S7, the determined endocardium contour 2 is then used in order to determine an epicardium contour enclosing the endocardium contour. For this purpose, the sufficiently extensively determined edge map is used once again, in the present case as a single cost map. The starting point is a typical initial radius for the epicardium which has been determined heuristically or based on prior anatomical knowledge, and which is of course greater than the radius of the endocardium. In the edge map, the edges of the endocardium segment are removed, an MCP algorithm with distance weighting once again being used in order to localize the epicardium contour, after which a smoothing can once again take place by determining the convex hull.

Since the endocardium contour and the epicardium contour are now known, there lies between the epicardium contour and the endocardium contour 2 the myocardium, in which contrast agent-enhanced picture elements can be identified based on threshold values and marked as contrast agent deposits, i.e. in particular scar tissue, which happens in step S8.

In a step S9, an output image can then be generated in which visualization elements indicating the endocardium contour 2, the epicardium contour and the scar tissue are added.

Figure 7:
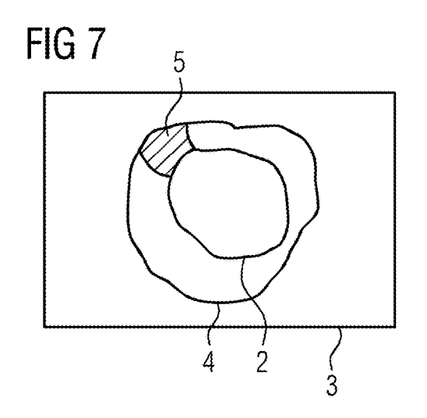
FIG. 7 shows an example of an output image.

FIG. 7 schematically shows an example of such an output image 3, in which for clarity of illustration, the actual image values of the magnetic resonance slice image are not shown. However, it can be clearly seen in the output image 3, due to corresponding visualization elements are the endocardium contour 2, the epicardium contour 4, and regions 5 having contrast agent deposits, in this case therefore scar tissue.

The steps described can be repeated for further magnetic resonance slice images if a slice stack is considered, in which case, of course, results from the first considered middle magnetic resonance slice image, for example in the form of initial values or with respect to the position of the center point of the left ventricle, can be applied or propagated to other magnetic resonance slice images.

Figure 8:
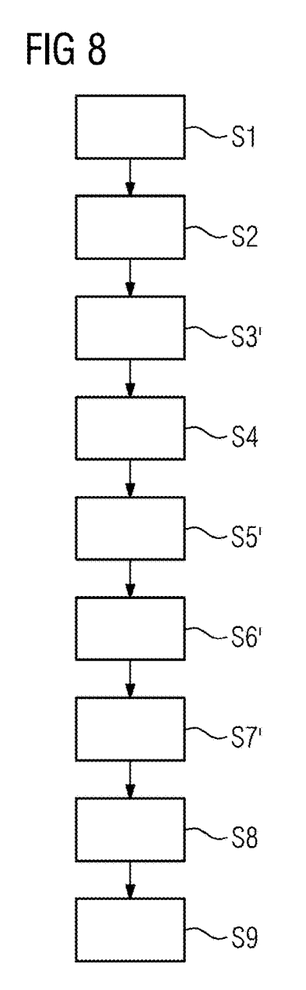
FIG. 8 is a flowchart of a second exemplary embodiment of the method according to the invention.

FIG. 8 shows a modified exemplary embodiment of the inventive method, which differs by no edge map being used, but rather a probability map is used, which was produced using an endocardium classifier and an epicardium classifier in each case. Therefore, that steps S3 and S5 to S7 have been replaced by steps S3' and S5' to S7'. In step S3', an endocardium classifier is applied to candidate picture elements in order to determine a probability with which said picture elements belong to the endocardium contour. The endocardium classifier is a trained random forest classification algorithm which evaluates sixteen locally determined properties with respect to the intensity and the gradient for the candidate picture elements and which has been trained by machine learning by annotated training data in which therefore the actual endocardium contour is known as a fundamental truth. In this case the candidate picture elements determine a search area which has been defined on the basis of the estimated contour 1. Starting from the center point of the left ventricle (and therefore the origin of the polar coordinate system), radial rays through the estimated contour 1 are considered, along which candidate picture elements are defined equidistantly in a meaningful, anatomically motivated search area, to which candidate picture elements the endocardium classifier is then to be applied.

Thus, if, in step S3', the endocardium classifier is applied to each of the candidate picture elements, a probability map is produced which describes for each candidate picture element a probability value for its belonging to the endocardium contour 2.

Figure 9:
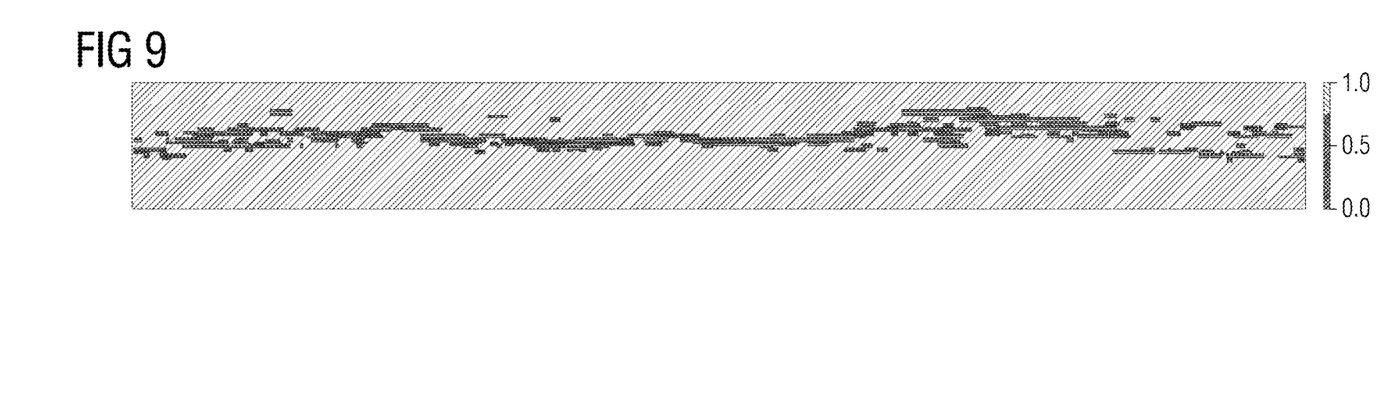
FIG. 9 shows an example of a probability map.

An exemplary probability map is depicted schematically in FIG. 9.

In step S5', the probability map and the deposition map of the (in this case unchanged) step S4 are then combined once again to form the cost map, wherein picture elements marked as potentially containing a contrast agent deposit again contain costs of one, while other picture elements contain costs of one minus the probability value. Similarly, in step S6', the MCP algorithm is once again performed as a path finding algorithm; in step S7', similarly to step S3', an analogously trained epicardium classifier is used in order to yield the basis for the search for the epicardium contour 4.

It should further be noted that it is also conceivable in the second exemplary embodiment to modify step S4 to produce a step S4' if the endocardium classifier is also embodied to indicate the probability with which a candidate picture element may be understood as revealing a contrast agent deposit.

Figure 10:
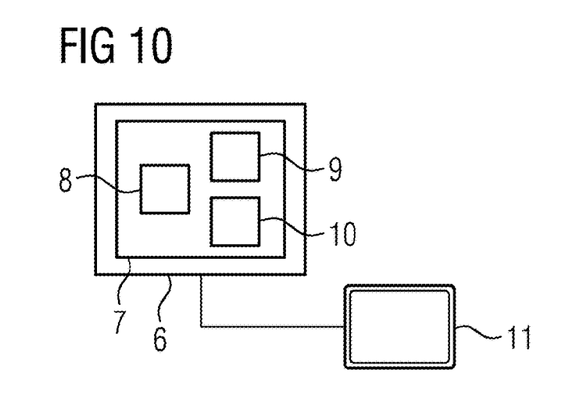
FIG. 10 is a block diagram of an image processor according to the invention.

Finally, FIG. 10 shows a simplified schematic diagram of an inventive image processing device 6 having a computer 7, which has at least one first determining unit 8 for detecting the endocardium contour 2, a second determining unit 9 for detecting the epicardium contour 4, and a marking unit 10 for marking picture elements revealing contrast agent deposit in the myocardium.

Further units and subunits may include a localization unit for detecting the left ventricle, various map determining units, an estimated contour finding unit, and a path finding unit. An output image generating unit may also be present in addition. The image processing device 6 may be connected to a display device 11 for visualizing the output image.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for evaluating a contrast agent-enhanced two-dimensional magnetic resonance slice image of a heart of a patient in order to determine picture elements in said slice image revealing contrast agent deposits in the myocardium of the heart, said method comprising:

providing a computer with a contrast agent-enhanced two-dimensional magnetic resonance slice image of a heart, said slice image being comprised of picture elements;

in said computer, determining an endocardium contour of the endocardium of the heart in the magnetic resonance slice image, using deposition information describing picture elements that are candidates for revealing contrast agent deposits, by executing an image analysis based on an assumption, provided to the computer, of a shape for a structure of the heart in the slice image and, in said image analysis, avoiding picture elements as components of said endocardium contour that are said candidates for revealing contrast agent deposits;

in said computer, determining an epicardium contour that encloses the endocardium contour;

in said computer, marking picture elements that indicate contrast agent enhancement in the myocardium lying between the epicardium contour and the endocardium contour, as contrast agent deposit; and making the slice image, with the picture elements marked as contrast agent deposit, available from the computer in electronic form, as a data file.

2. A method as claimed in claim 1 comprising, in said image analysis in said computer, using a shape assumption for the left ventricle of the heart, as said assumption of the shape of said heart structure.

3. A method as claimed in claim 1 comprising determining said endocardium contour and said epicardium contour by localizing said heart structure using background information describing said structure as having a circular shape, as said assumption of said shape.

4. A method as claimed in claim 3 comprising detecting said structure in said image analysis using at least one of circular Hough transforms and a circularity measure of said circular shape.

5. A method as claimed in claim 1 comprising determining said endocardium contour by first determining an estimated endocardium contour by localization of blood within said structure, and using said estimated contour to determine said deposition information.

6. A method as claimed in claim 5 comprising determining said estimated endocardium contour by executing a morphological active evolution algorithm for a contour curve.

7. A method as claimed in claim 6 comprising executing said morphological active evolution algorithm for a contour curve without taking edges into consideration.

8. A method as claimed in claim 5 comprising determining said deposition information by first defining an inner region within said estimated endocardium contour and an outer region surrounding the estimated endocardium contour, and marking picture elements in the outer region, as representing contrast agent deposit, which exceed a threshold value determined by statistical evaluation of values of the picture elements in said inner region.

9. A method as claimed in claim 5 comprising identifying candidate picture elements, from said estimated endocardium contour, for inclusion as contour points in said endocardium contour, by equidistant point selection along radial rays with respect to said structure, and applying an endocardium classifier to each candidate picture element that produces an output, for each candidate picture element applied to said endocardium classifier, comprising at least one of a value describing whether the respective candidate picture elements represents contrast agent deposit, and a value representing a probability that the respective candidate picture element belongs said endocardium contour.

10. A method as claimed in claim 9 comprising operating said endocardium classifier according to a classification algorithm trained by machine learning, using training slice images as training data that contain fundamental truths for said classification algorithm.

11. A method as claimed in claim 10 comprising using a random forest algorithm as said classification algorithm.

12. A method as claimed in claim 9 comprising operating said endocardium classifier to evaluate at least one property of each candidate picture element selected from the group consisting of an intensity of the respective candidate picture element, a gradient of the respective candidate picture element, and an environment in said slice image that encompasses the candidate picture element.

13. A method as claimed in claim 1 comprising determining said endocardium contour by:

applying an endocardium classifier to candidate picture elements for inclusion as contour points of said endocardium contour, that produces an output value, for each candidate picture element, describing a probability of the respective candidate picture element being a contour point of said endocardium contour; and determining a cost map that designates candidate picture elements having a probability value above a predetermined value and avoiding candidate picture elements, according to said deposition information, that represent contrast agent deposits, and using said cost map to define picture elements, among said candidate picture elements for inclusion in said endocardium contour.

14. A method as claimed in claim 13 comprising determining said cost map by one of:

executing a pathfinding algorithm with path length weighting in order to identify a minimum cost path as said cost path; and using a polar coordinate system referenced to a centerpoint of said structure in order to search for a path along a polar angle that is shortest.

15. A method as claimed in claim 1 comprising:

in said computer, determining edge information describing a position of edges in said magnetic resonance slice image; and determining said endocardium contour by applying a cost map to said edge information in order to identify path preferring edges, while avoiding picture elements representing contrast agent deposits, in order to identify picture elements for inclusion in said endocardium contour.

16. A method as claimed in claim 15 comprising determining said cost map by one of:

executing a pathfinding algorithm with path length weighting in order to identify a minimum cost path as said cost path; and using a polar coordinate system referenced to a centerpoint of said structure in order to search for a path along a polar angle that is shortest.

17. A method as claimed in claim 1 wherein providing said computer with said contrast agent-enhanced two-dimensional magnetic resonance slice image comprises one of providing said computer with a short-axis magnetic resonance slice image, and providing said computer with a plurality of magnetic resonance slice images of a slice image stack covering the heart from the base to the apex.

18. A method as claimed in claim 1 comprising, at a display in communication with said computer, displaying said magnetic resonance slice image with said picture elements marked as contrast agent deposit having a different visual appearance than other picture elements in the displayed magnetic resonance slice image.

19. An image processing computer comprising:

a processor;

said processor having an input that receives a contrast agent-enhanced two-dimensional magnetic resonance slice image of a heart, said slice image being comprised of picture elements;

said processor being configured to determine an endocardium contour of the endocardium of the heart in the magnetic resonance slice image, using deposition information describing picture elements that are candidates for revealing contrast agent deposits, by executing an image analysis based on an assumption, provided to the computer, of a shape for a structure of the heart in the slice image and, in said image analysis, avoiding picture elements as components of said endocardium contour that are said candidates for revealing contrast agent deposits;

said processor being configured to determine an epicardium contour that encloses the endocardium contour;

said processor being configured to mark picture elements that indicate contrast agent enhancement in the myocardium lying between the epicardium contour and the endocardium contour, as contrast agent deposit; and said processor being configured to make the slice image, with the picture elements marked as contrast agent deposit, available as an output of the processor in electronic form, as a data file.

20. A non-transitory, computer-readable data storage medium encoded with programming instructions, said storage medium being loaded into an image processing computer and said programming instructions causing said image processing computer to:

receive a contrast agent-enhanced two-dimensional magnetic resonance slice image of a heart, said slice image being comprised of picture elements;

determine an endocardium contour of the endocardium of the heart in the magnetic resonance slice image, using deposition information describing picture elements that are candidates for revealing contrast agent deposits, by executing an image analysis based on an assumption, provided to the computer, of a shape for a structure of the heart in the slice image and, in said image analysis, avoiding picture elements as components of said endocardium contour that are said candidates for revealing contrast agent deposits;

determine an epicardium contour that encloses the endocardium contour;

mark picture elements that indicate contrast agent enhancement in the myocardium lying between the epicardium contour and the endocardium contour, as contrast agent deposit; and make the slice image, with the picture elements marked as contrast agent deposit, available from the computer in electronic form, as a data file.

* * * * *